United States Patent [19]
Bhaduri et al.

[11] 4,393,244
[45] Jul. 12, 1983

[54] METHOD AND THE MANUFACTURE OF CYCLIC MONO AND/OR DIKETONES FROM CYCLIC MONO OR SESQUI TERPENES BY CATALYTIC OXIDATION

[75] Inventors: Sumit Bhaduri; Madan M. Mahandru, both of Maharashtra, India

[73] Assignee: Indian Explosives Limited, Calcutta, India

[21] Appl. No.: 296,280

[22] Filed: Aug. 26, 1981

[51] Int. Cl.³ .............................................. C07C 45/34
[52] U.S. Cl. ................................ 568/360; 252/431 P; 252/431 N
[58] Field of Search ............... 568/357, 360, 401, 400; 252/431 P, 431 N

[56] References Cited

U.S. PATENT DOCUMENTS

| | | | |
|---|---|---|---|
| 2,690,457 | 9/1954 | Hackmann | 568/401 |
| 2,992,272 | 7/1961 | Hay | 568/360 |
| 3,259,638 | 7/1966 | Allison | 568/260 |
| 3,361,807 | 1/1968 | Duncanson et al. | 568/360 |
| 3,847,993 | 11/1974 | Hall et al. | 568/360 |
| 3,857,900 | 12/1974 | Wilkinson | 252/431 P |
| 4,288,380 | 9/1981 | Billig et al. | 252/431 P |

Primary Examiner—James H. Reamer
Attorney, Agent, or Firm—Ladas & Parry

[57] ABSTRACT

Cyclic terpenes containing at least one unsubstituted methylene group adjacent to a double bond are converted into cyclic mono- and/or diketones by oxidation with oxygen in the presence of a transition metal catalyst.

10 Claims, No Drawings

METHOD AND THE MANUFACTURE OF CYCLIC MONO AND/OR DIKETONES FROM CYCLIC MONO OR SESQUI TERPENES BY CATALYTIC OXIDATION

The present invention relates to a novel method for the manufacture of mono and/or diketonic derivatives. In particular, it relates to a method for the selective manufacture of mono and/or diketonic derivatives of mono or sesqui terpenic olefins by catalytic oxidation.

Of the many substrates which have been oxidised in the presence of transition metal complexes, one of the most extensively studied group or organic compounds has been olefin hydrocarbons. Surprisingly, no attempt has so far been made to invent similar methods for selective oxidation of terpenic olefins to oxygen containing products.

The object of the present invention is to provide a method for selective oxidation of terpenic olefins to oxygen containing products.

A further object of the invention is to produce value-added chemicals by the conversion of the oxygenated products of the invention.

The advantage of the present invention is apart from providing the oxygenated products, it also opens up the possibility of further functionalisation of the parent olefins. The oxygenated products in most of the cases could be converted to value-added chemicals. Thus, 2,6,6$_o$-trimethyl bicyclo(3,1,1)hept-2-en-4-one could be converted to thymol by a simple catalytic dehydrogenation.

The method according to the present invention consists in oxidation with oxygen or oxygen containing gas such as air, of the mono or sesqui terpenic olefins with co-ordination or organometallic complexes of V, Cr, Mn, Fe, Rh, Co, Cu, Ir, Ni, Pd, Pt and Cu. The olefins should satisfy one important condition, namely one or both of the allylic positions should be unsubstituted. Obviously, for a diketonic derivative, both such positions will have to be unsubstituted whereas for a monoketonic derivative at least one allylic position should be unsubstituted.

Accordingly, the invention provides a process for the preparation of cyclic mono and/or diketones which comprises reacting a cyclic mono or sesquiterpenoid hydrocarbon containing at least one unsubstituted methylene group adjacent to a double bond with oxygen or an oxygen containing gas in the presence of a catalyst selected from the carboxylate salts and co-ordination and organometallic complexes of a transition metal. The following diagram illustrates some of these conversions:

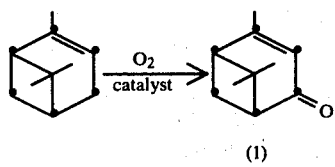

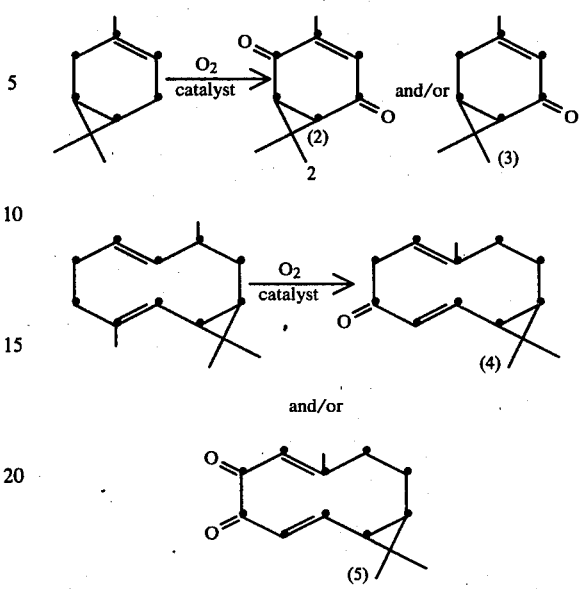

Although some conversions to a mixture of mono- and diketonic derivatives could be effected by complexes of all the metals listed above for high conversions and selectivities, the preferred metals are Mn(II) or Mn(III), Co(II) or Co(III), Cu(I) or Cu(II) and Fe(II) or Fe(III). The reactions presumably proceed through the well-known Haber-Weiss mechanism of radical auto-oxidation.

It is known that under the conditions used for similar oxidations of olefins the original ligand environment of the metal ion does not remain unchanged. The effectiveness of the catalyst partly depends on its solubility and, therefore, any soluble compound of the preferred metals should be able to initiate and propagate the radical auto-oxidation in varying degree. Apart from the carboxylates such as stearates, oleates, acetates and benzoates of Co(II or III), Mn(II or III) and Cu(I or II) which have been widely used for the other olefin oxidation reactions, the catalysts could be any or more of the compounds represented by the formulae A, B, C and D as depicted below:

$$M_m(L_2)_nX_p(O)_q \qquad \text{Formula A}$$

where
L$_2$=2,2'bipyridyl or substituted 2,2'bipyridyl or substituted or unsubstituted 1,10-orthophenanthroline; and (a) M=Cu, m=2, n=2, X=J, Br or cl and p=2, q=0 or
(b) M=Cu, m=1, n=1, X=NO$_2$, p=2, q=0 or
(c) M=Mo, m=1, n=1, X=Br, p=2, q=2

$$M(O)_m[(R_1CO)CH(COR_2)]_n \qquad \text{Formula B}$$

where,
(a) M=V, m=1, n=2, R$_1$ and R$_2$ which may be the same or different, represent CH$_3$, C$_2$H$_2$, n-C$_3$H$_7$, CF$_3$, C$_6$H$_5$, C$_6$H$_5$CH$_2$, or,
(b) M=Mo, m=2, n=2, R$_1$ and R$_2$ as shown in (a) or,
(c) M=Co, m=0, n=2, R$_1$ and R$_2$ as shown in (a) or,
(d) M=Co, m=0, n=3, R$_1$ and R$_2$ as shown in (a) or,
(e) M=Mn, m=0, n=2 as shown in (a) or, (f) M=Cu, m=0, n=2 as shown in (a) or,
(g) M=Rh, m=0, n=3 as shown in (a); M=Fe, M=0, n=3 as shown in (a)

$$ML_nX_p \qquad \text{Formula C}$$

where,
(a) M=Rh, L=PPH$_3$, n=3, X=Cl, p=1 or,
(b) M=Rh, L=PPH$_3$, n=3, X=Cl, p=2

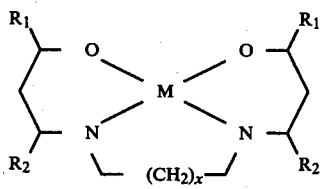

Formula D where,
M=Co, x=2 or 3, R$_1$ and R$_2$ which may be same or different and represent CH$_3$, C$_2$H$_5$, C$_3$H$_7$, CF$_3$, Ph, PhCH$_2$.

The oxidation reactions can be effected at temperature ranging from 0° C. to about 250° C. and preferably at ambient room temperature upto about 100° C. Both air or pure oxygen could be used as the oxidising agent. The pressures employed are in the range of atmospheric to 1000 psi. Optimisation of temperature and pressure is required depending on the substrate involved, and the desired ratio of the mono- to diketonic derivatives.

The residence time of the reactions can be followed by taking periodic gas-chromatographic samples of the product mixture. The products are first isolated by chromatographic techniques and structures established by the usual spectroscopic methods. These are then used for rapid gas-chromatographic analysis. The reaction time varies with the desired ratio of mono- to diketonic derivatives, the pressure employed, the temperatures used and the like considerations.

In the practice of these processes neat terpenic olefins are preferably used but they could also be diluted with solvents. The solvents employable include by way of example carbon tetrachloride, benzene, n-octane, decadin and ethyl acetate.

The following examples are given by way of illustration of the invention without limiting the scope of the invention in any way:

EXAMPLE 1

α-pinene (15 parts) was contacted with 2,2'-dipyridyl cuprous iodide dimer (0.5 part) at 50° C. under air at a pressure of 100 psi for 600 minutes. The reaction mixture was vigorously stirred. The products were analysed by gas liquid chromatography showing 40% conversion of α-pinene to the corresponding mono-ketone derivative (1) in the diagram.

EXAMPLE 2

Δ$^3$-carene (20 parts) was contacted with bis (pentane-2,4-dionato) cobalt (II) (0.2 part) under 50 psi of oxygen for 60 minutes. The reaction mixture was vigorously stirred. The products were analysed by gas liquid chromatography showing 75% conversion of Δ$^3$-carene. The converted material consisted of the 5-ketocarene (60%), 2,5-diketo-carene (10%) and other products (5%).

EXAMPLE 3

Δ$^3$-carene (20 parts) was contacted with cobalt (II) stearate (0.5 part) under 250 psi of oxygen at 80° C. for 24 hours. The reaction mixture was vigorously stirred. The products were analysed by gas-liquid chromatography showing 95% conversion of Δ$^3$-carene. The converted material consisted of the 5-ketocarene (30%), 2,5-diketocarene (50%) and other products (15%).

EXAMPLE 4

Bicyclogeracrene (25 parts) was contacted with manganese (II) acetate (1 part) at 120° C. under an oxygen pressure of 400 psi. The reaction mixture was vigorously stirred for 12 hours. The products were analysed by gas-liquid chromatography showing 60% conversion of which the diketone and the monoketone (5) and (4) in the diagram were of 50% and 5%.

We claim:
1. A process for the preparation of cyclic mono and/or diketones which comprises reacting a cyclic mono or sesquiterpenoid hydrocarbon containing at least one unsubstituted methylene group adjacent to a double bond with oxygen or an oxygen containing gas in the presence of a catalyst selected from the group consisting of compounds of the formulas:

$$M_m(L_2)nX_p(O)_q$$

where
L$_2$ is 2,2'-bipyridyl or 1,10-orthophenanonthroline, and either
(a) M is Cu, m=2, X is I, Br or Cl, p=2, q=0; or
(b) M is Cu, m=1, n=1, X is NO$_2$, p=2 and q=0; or
(c) M is Mo, m=1, n=1, X=Br, p=2 and q=2;

$$R''L_3Cl$$

where
L is triphenylphosphine;

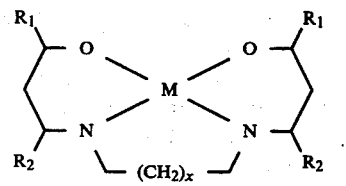

where
M is Co, X=2 to 3 and R$_1$ and R$_2$ which may be the same or different represent methyl, ethyl, propyl, trifluoromethyl, phenyl or benzyl; and $$M(O)_m[(R_1CO)CH(COR_2)]_n$$

where
R$_1$ and R$_2$ which may be the same or different represent methyl, ethyl, n-propyl, trifluoromethyl, phenyl or benzyl, and
(a) M is V, m=1, n=2, or
(b) M is Mo, m=2, n=2, or
(c) M is Co, m=o, n=2, or
(d) M is Co, m=o, n=2, or
(e) M is Mn, m=o, n=2, or
(f) M is Cu, m=o, n=2, or
(g) M is Rh, m=o, n=3, or
(h) M is Fe, m=o, n=3.

2. A process as claimed in claim 1, in which the oxygen containing gas is air.

3. A process as claimed in claim 1 or claim 2, wherein the reaction is conducted at from 0° C. to about 250° C.

4. A process as claimed in claim 3, wherein the temperature is from about ambient room temperature to about 100° C.

5. A process as claimed in claim 3, wherein the reaction is conducted at a pressure of from 1 atmosphere to 1000 psi.

6. A process as claimed in claim 5, wherein the pressure is from 50–400 psi.

7. A process as claimed in claim 4, in which the reaction is conducted in the presence of an inert liquid diluent.

8. A process as claimed in claim 1, wherein α-pinene is converted to 2,6,6-trimethylbicyclo(3,1,1)hept-2-en-4-one.

9. A process as claimed in claim 1, wherein $\Delta^3$-carene is converted to 3,7,7-trimethylbicyclo(4,1,0)hept-3-en-5-one and/or 3,7,7-trimethylbicyclo(4,1,0)hept-3-en-2,5-dione.

10. A process as claimed in claim 1, wherein bicyclogeracrene is converted to 4,11,11-trimethylbicyclo(8,1,0)undec-4,8-dien-7-one and/or 4,11,11-trimethylbicyclo(8,1,0)undec-4-8-dien-6,7-dione.

* * * * *